United States Patent [19]
Itoigawa et al.

[11] Patent Number: 6,019,729
[45] Date of Patent: Feb. 1, 2000

[54] SENSOR MECHANISM-EQUIPPED CATHETER

[75] Inventors: Kouichi Itoigawa; Hitoshi Iwata, both of Niwa, Japan

[73] Assignee: Kabushiki Kaisha Tokai-Rika-Denki-Seisakusho, Toyota, Japan

[21] Appl. No.: 08/970,610

[22] Filed: Nov. 14, 1997

[30] Foreign Application Priority Data

Nov. 15, 1996 [JP] Japan ................................. 8-304980
Nov. 15, 1996 [JP] Japan ................................. 8-304981

[51] Int. Cl.$^7$ ................................................. A61B 5/02
[52] U.S. Cl. ...................... 600/488; 600/481; 600/485; 600/486
[58] Field of Search ........................... 600/481, 485, 600/486, 487, 488, 497

[56] References Cited

U.S. PATENT DOCUMENTS

| | | | |
|---|---|---|---|
| 3,565,056 | 2/1971 | Statham | 600/488 |
| 3,946,724 | 3/1976 | La Balme | 600/488 |
| 5,755,668 | 5/1998 | Itiogawa et al. | 600/488 |
| 5,807,265 | 9/1998 | Itiogawa et al. | 600/486 |
| 5,836,886 | 11/1998 | Itiogawa et al. | 600/488 |

*Primary Examiner*—Cary O'Connor
*Assistant Examiner*—Navin Natnithithadha
*Attorney, Agent, or Firm*—Oliff & Berridge, PLC

[57] ABSTRACT

A sensor mechanism-equipped catheter is easy to produce, suitable for a diameter reduction, and achieves a high sensing precision. In a catheter, a sensor assembly has a pressure-receiving piston, a pressure-transmitting silicon gel or oil and a pressure sensor chip, and is fitted to a distal end of a catheter tube. The sensor assembly detects a pressure change. The sensor assembly further has an outer tube that carries the piston at a distal end side thereof, and an inner tube carrying the sensor chip an end side thereof. A space formed in the outer tube, between the piston and the sensor chip, is filled with the silicone gel or oil. A pressure barrier wall is provided for blocking flow of the silicone gel toward the catheter tube. The sensor chip is fixed in the sensor assembly by a joining member which divides an interior space of the sensor assembly into a distal end-side region and a base end-side region. The joining member may also serve as the pressure barrier wall.

20 Claims, 8 Drawing Sheets

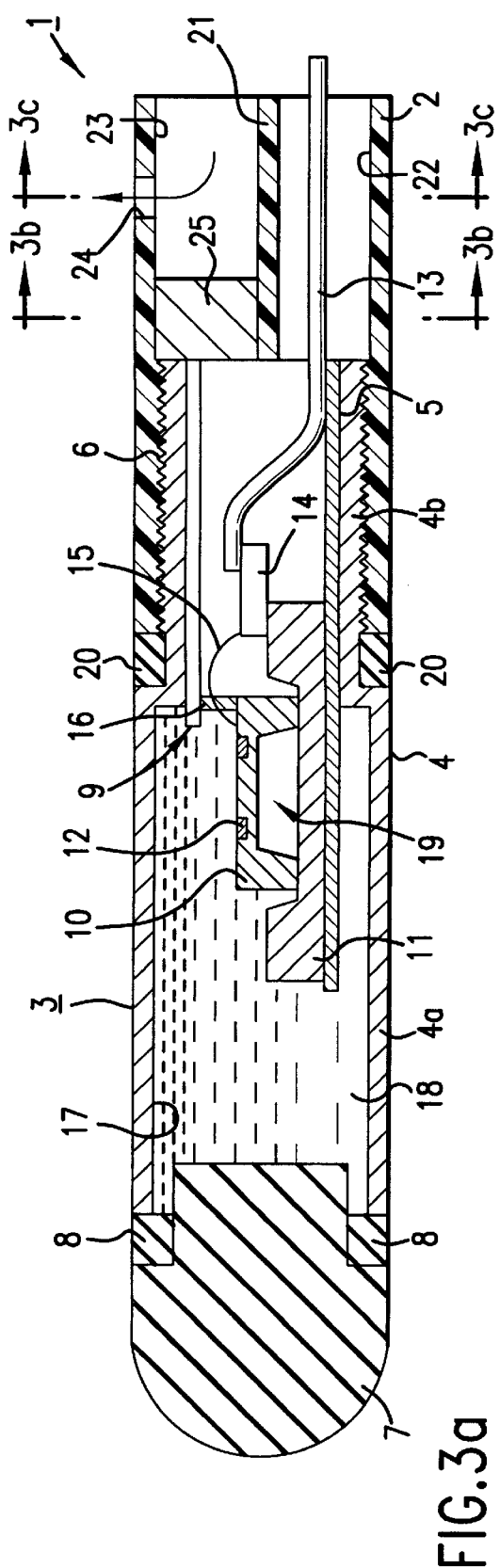
FIG.3a
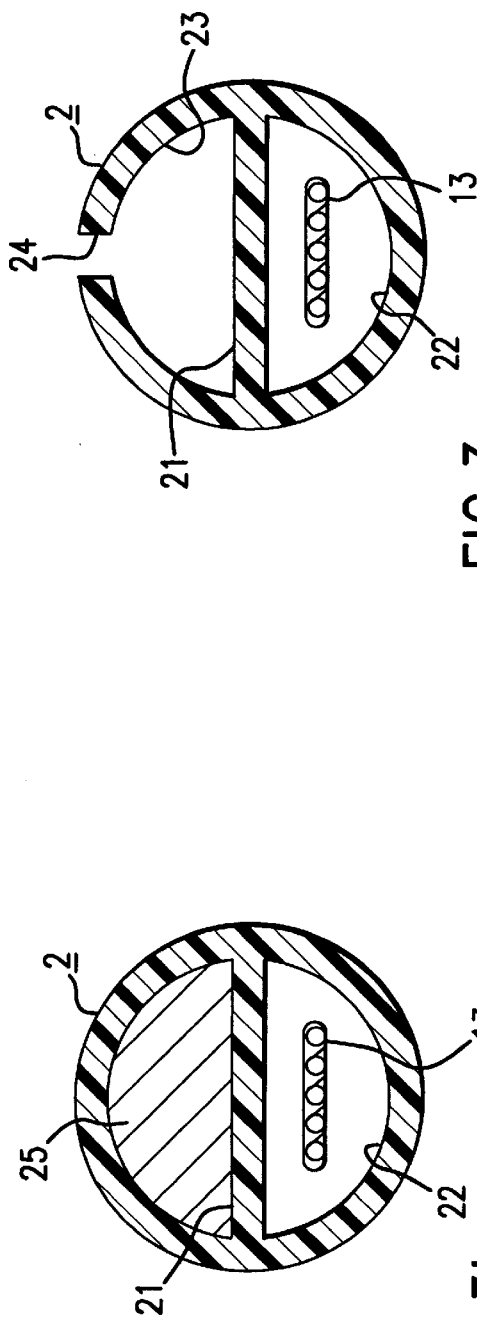
FIG.3c
FIG.3b

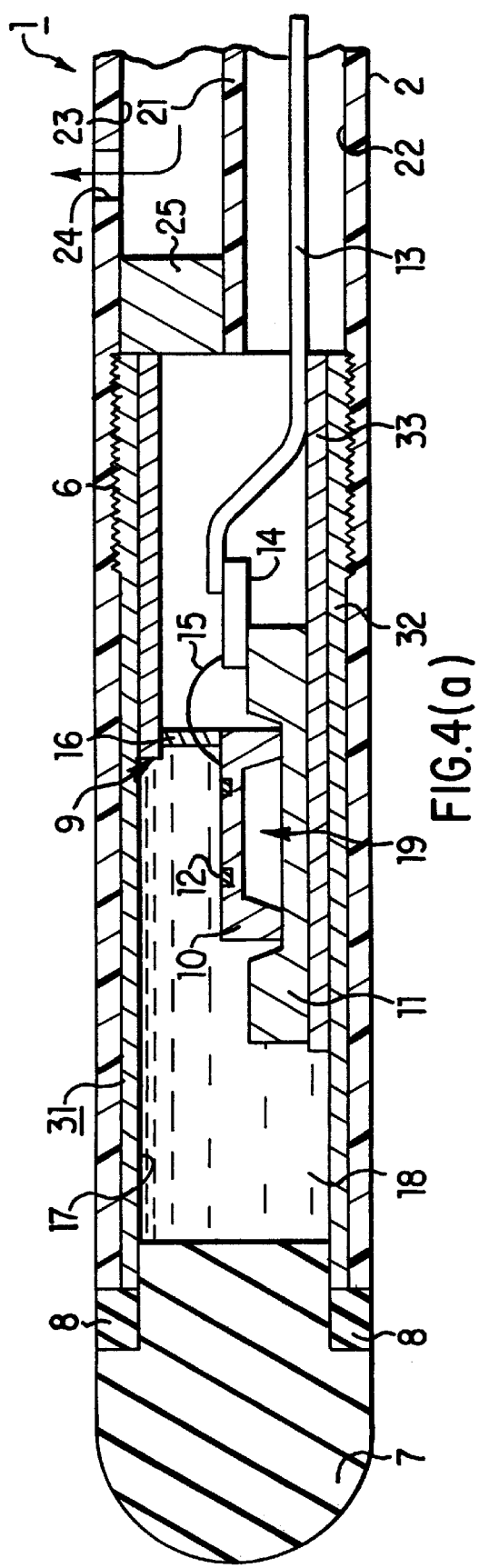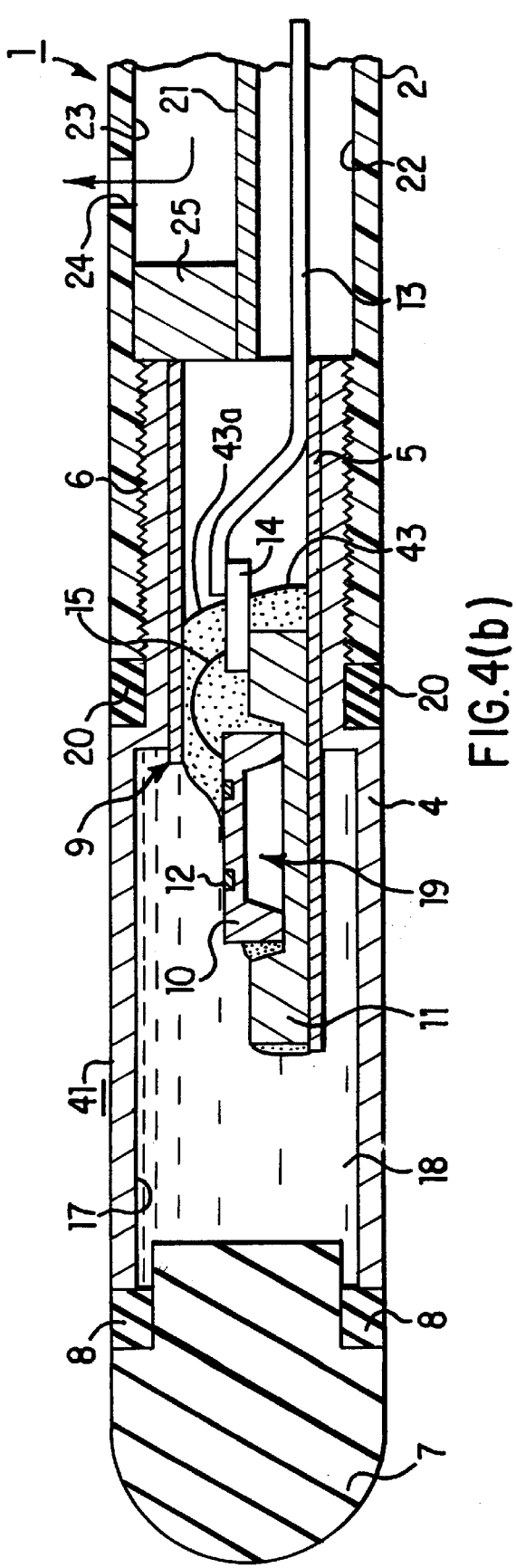

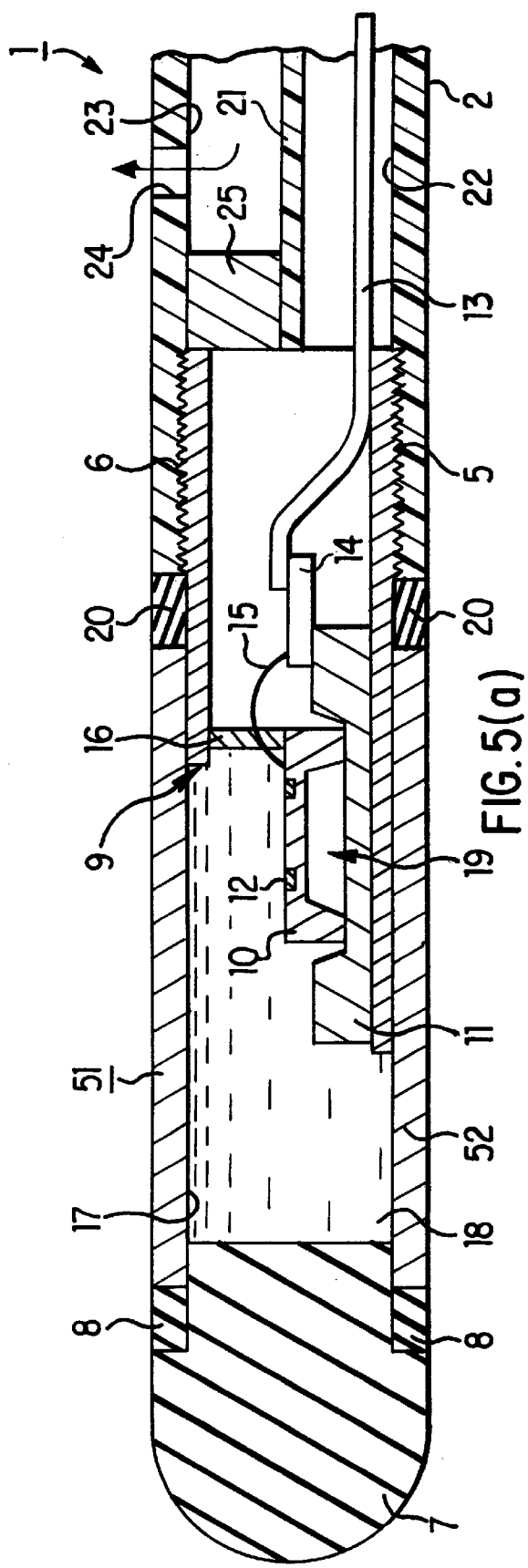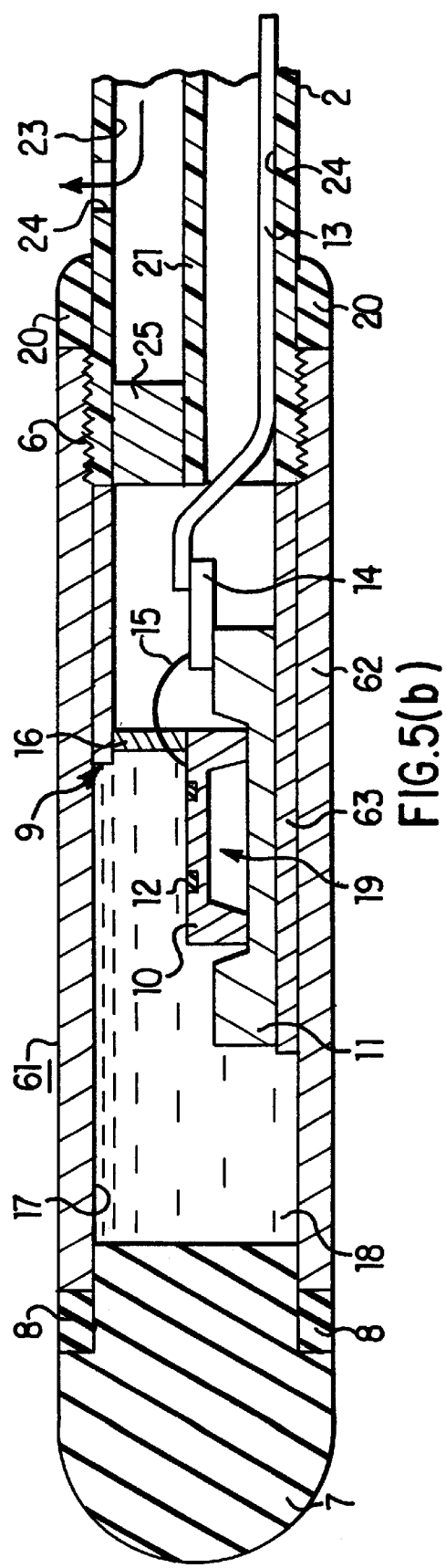

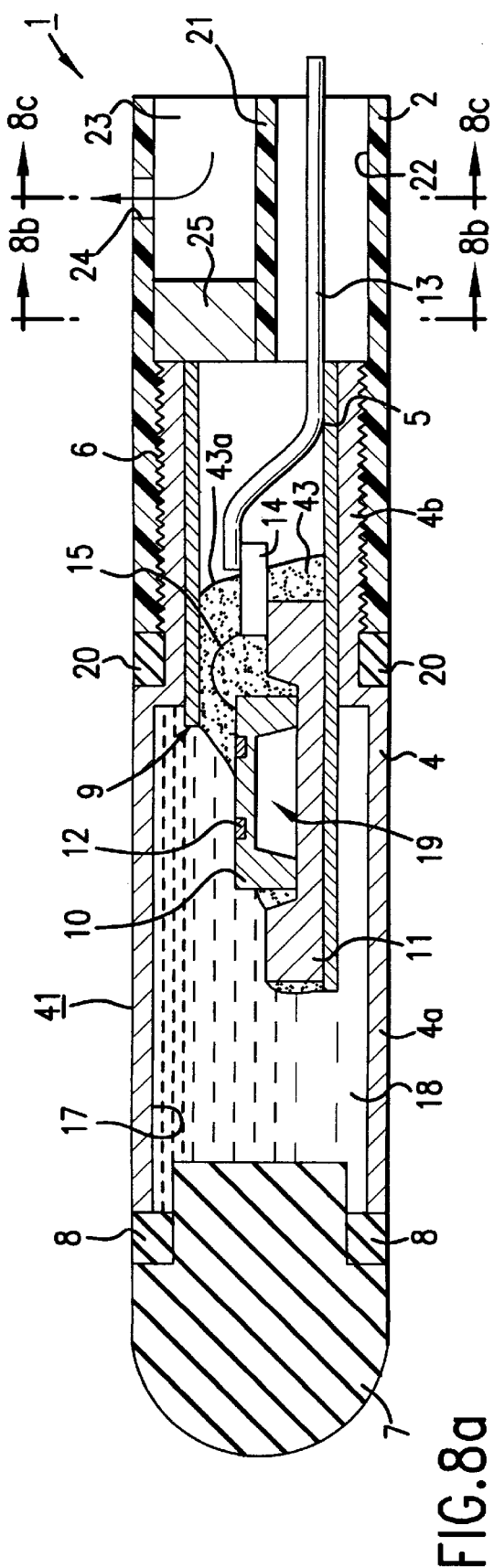
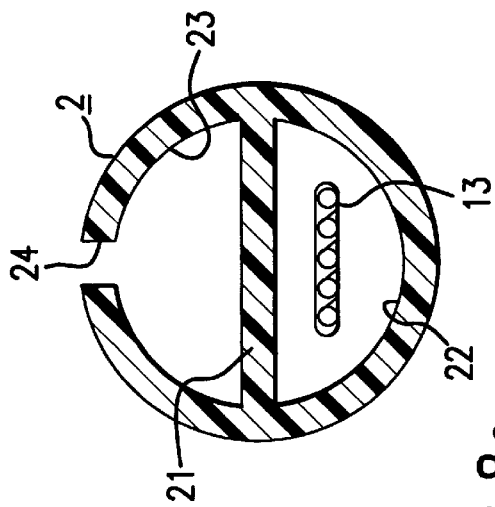
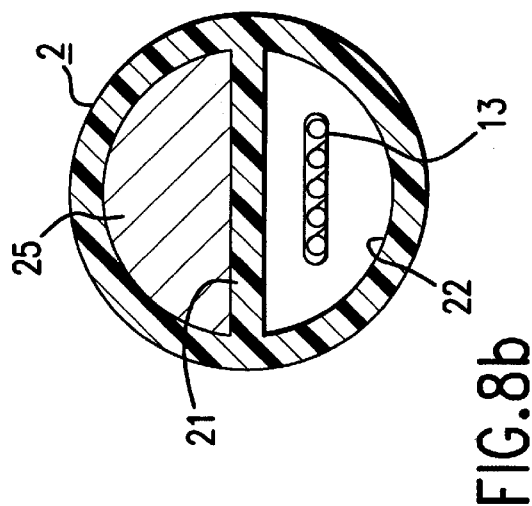
FIG. 8a
FIG. 8b
FIG. 8c

SENSOR MECHANISM-EQUIPPED CATHETER

The entire disclosures of Japanese Patent Application Nos. Hei 8-304981 and Hei 8-304980 both filed on Nov. 15, 1997 including the specifications, drawings and abstracts are incorporated herein by reference.

BACKGROUND OF THE INVENTION

1. Field of the Invention

The present invention relates to a sensor mechanism-equipped catheter having a sensor portion that is disposed on a distal end of a catheter tube insertable into a living body.

2. Description of the Related Art

A catheter is a well-known medical tubular device for insertion into a body. A catheter tube, that is, a component of the catheter, has a diameter of at most several millimeters and is insertable into various passageways in a body, for example, blood vessels. In operation, a distal end of the catheter tube is guided to a desired site in a body, where a measurement (for example, blood pressure measurement and the like) or a curing operation (for example, vascular expansion and the like) is performed. Therefore, an operator of a catheter needs to unfailingly guide the distal end of the catheter tube to a desired site through external control.

Body passageways are not necessarily straight. Many passageways locally bend or divide into branches. Furthermore, body passageways are not necessarily consistent in diameter. The tube diameters of passageways may decrease, or an obstacle (for example, a blood clot) may exist in a passageway, thereby reducing the passageway diameter. Therefore, a conventional catheter having no device for detecting a situation or condition ahead in the moving direction of the catheter tube requires an operator to rely on the operator's experienced skill in order to properly operate the tube, that is, to guide the tube to a desired site.

To solve such a drawback, sensor mechanism-equipped catheters have been proposed. An example of conventional sensor mechanism-equipped catheters is shown in FIG. 10. In a sensor mechanism-equipped catheter 91, a catheter tube 92 has a pressure barrier wall 93 that is provided near a distal end of the catheter tube 92. A chip-housing chamber 94 is thereby separately formed inside the tube 92. The pressure barrier wall 93 is normally formed of a stainless steel or ceramic plate material. In the chip-housing chamber 94, a semiconductor pressure sensor chip 96 is mounted on a seat member 95 fixed in the chamber 94. The chip-housing chamber 94 is filled with a pressure-transmitting medium 97. A piston 98 for sealing the pressure-transmitting medium 97 is disposed movably on a distal end opening of the tube 92.

In the sensor mechanism-equipped catheter 91, when a pressure change occurs on the outside surface of the piston 98, which is a pressure-receiving portion, the effect of the pressure change is transmitted to the pressure-sensitive surface of the sensor chip 96 by the pressure-transmitting medium 97. In this manner, the presence of an obstacle or the like in the moving direction of the catheter tube 92 can be detected.

However, in the conventional sensor mechanism-equipped catheter 91, the catheter tube 92 has a small diameter, so that it is difficult to incorporate various small-size components, such as the sensor chip 96, the seat member 95, the pressure barrier wall 93 and the like, into the tube 92. Thus, the production of the conventional catheter 91 is not easy. Furthermore, since the aforementioned special components must be mounted in the tube 92, a normal catheter tube cannot be employed but a dedicated catheter tube must be prepared.

Normally, smaller diameters of catheters are more favorable. However, the smaller the diameter of the catheter tube 92, the more difficult it becomes to mount in the tube 92 the pressure barrier wall 93 that can reliably block flow of the pressure-transmitting medium 97. The production thus becomes more difficult. If the pressure barrier wall 93 may be able to be mounted inside the tube 92 with a reduced diameter, it is likely that a gap will form between the wall 93 and the tube 92 or the like, thereby failing to reliably sealing in the tube interior. If this happens, the pressure-transmitting medium 97 is allowed to flow toward the base end of the tube 92, so that precise pressure transmission becomes impossible and the sensing precision of the catheter 91 deteriorates. Due to this problem, size reduction must be traded for improvements in sensing precision of the conventional catheter.

SUMMARY OF THE INVENTION

Accordingly, it is an object of the present invention to provide a sensor mechanism-equipped catheter that is easy to produce.

It is another object of the invention to provide a sensor mechanism-equipped catheter achieving a high sensing precision and having a construction suitable for a size reduction.

It is still another object of the invention to provide a sensor mechanism-equipped catheter that is easy to produce, robust against failures, and suitable for use in vivo.

According to one aspect of the invention, there is provided a sensor mechanism-equipped catheter including a catheter tube, and a sensor portion disposed at a distal end side of the catheter tube, for detecting a pressure change. The sensor portion includes a pressure-receiving portion, a pressure-sensing portion, an outer tube holding the pressure-receiving portion at a distal end side of the outer tube, and an inner tube supporting the pressure-sensing portion at an end side of the inner tube. The inner tube is fitted into the outer tube. A pressure-transmitting medium fills a space between the pressure-receiving portion and the pressure-sensing portion. The space is formed within the outer tube. The sensor portion further includes a pressure barrier wall that prevents the pressure-transmitting medium from flowing toward the catheter tube.

In the sensor mechanism-equipped catheter, the pressure-sensing portion of the sensor portion can be disposed at any desired position by securing the pressure-sensing portion to an end side of the inner tube, and then inserting the inner tube into the outer tube. Therefore, the sensor mechanism-equipped catheter of the invention is easy to produce.

The sensor portion may be provided as a unit separate from the catheter tube, and may be mounted at the distal end side of the catheter tube.

A desired catheter can be obtained simply by mounting the sensor portion, which has been provided a separate component, to a distal end side of the catheter tube. Thus, the sensor mechanism-equipped catheter is easy to produce, distinguished from the conventional art, wherein the components constituting a sensor portion are directly mounted in a catheter tube At least one of the outer tube and the inner tube may have an irregular surface that is formed in a joint portion thereof fittable to the distal end side of the catheter tube.

The irregular surface formed on the joint portion the outer tube and/or the inner tube increases the resistance on the interface with the catheter tube and, therefore, substantially inhibits the sensor portion from slipping off from the catheter tube.

The sensor mechanism-equipped catheter of the invention may also be constructed as follows. The joint portion is formed as a base end-side small-diameter portion of the outer tube, and a plurality of slip-off preventative grooves extend, in a circumferential direction, on an outer peripheral surface of the small-diameter portion.

The slip-off preventative grooves formed on the small-diameter portion of the outer tube, which is the joint portion, increases the resistance on the interface with the catheter tube and, therefore, substantially prevents the sensor portion from slipping off from the catheter tube.

A biologically compatible material may be used to form a component of the sensor portion that is externally exposed.

Use of a biologically compatible material in forming a component of the sensor portion exposed externally helps realize a sensor mechanism-equipped catheter that is highly compatible with human and animal bodies, and the like.

The sensor portion may be joined to the catheter tube by an adhesive that is made of a biologically compatible material.

Use of a biologically compatible adhesive to join the sensor portion to the catheter tube ensures reliable prevention of the sensor portion from slipping off from the catheter tube and, furthermore, helps realize a sensor mechanism-equipped catheter that is highly compatible with human and animal bodies, and the like.

According to another aspect of the invention, there is provided a sensor mechanism-equipped catheter including a catheter tube, and a sensor portion disposed at a distal end side of the catheter tube, for detecting a pressure change. The sensor portion includes a pressure-receiving portion, a pressure-transmitting medium, a pressure sensing device, and a joining member for fixing the pressure sensing device in the sensor portion. The joining member has been formed by disposing a fluidal material and hardening the fluidal material. The joining member also serves as a pressure barrier wall that prevents the pressure-transmitting medium from flowing toward a base end of the catheter tube.

If the pressure barrier wall is formed by the joining member formed by disposing a fluidal material and hardening the material, it becomes possible to reliably seal an interior portion of a catheter tube, even if it has a small diameter, without allowing a gap to form, in comparison with a conventional solid pressure barrier wall. Thus, this construction contributes to diameter reduction of a catheter. Since the thus-formed pressure barrier wall blocks flow of the pressure-transmitting medium in a direction toward the tube base end, pressure escape in that direction is prevented. Therefore, the difference between an increase in the pressure acting on the pressure-receiving portion and the corresponding increase in the pressure of the pressure-transmitting medium is reduced, so that an accurate pressure can be transmitted to the pressure sensing device. The sensing precision thereby improves. Furthermore, since the joining member also serves as a pressure barrier wall, the number of component parts is correspondingly reduced, thereby leading to a cost reduction.

The sensor portion may further include a tube member that has been formed separately from the catheter tube and that is fitted to a distal end side of the catheter tube. In this construction, the pressure sensing device is fixed to an inner wall surface of the tube member by the joining member, and the joining member seals a through bore of the tube member in such a manner that communication across the joining member is prevented.

If the sensor portion including the tube member is formed as a separate member, a sensor mechanism-equipped catheter according to the invention can be formed simply by fitting the sensor portion to a distal end portion of an existing catheter tube. Unlike a conventional catheter in which the individual components of a sensor portion are directly mounted in the catheter tube, the sensor mechanism-equipped catheter with this construction is easy to produce.

The pressure sensing device may include a semiconductor pressure sensor chip that is mounted on a seat member so that the sensor chip is fixed relative to a cut-out portion formed at a distal end side of the tube member.

If the semiconductor pressure sensor chip of a very small size is used as a pressure sensing device, the sensor portion can be reduced in diameter, compared with cases where the pressure sensing device is constructed in other manners. The construction employing a semiconductor pressure sensor chip is also more practical. Furthermore, with the cut-out portion formed at a distal end side of the tube member, it becomes relatively easy to fix the seat member, which carries the sensor chip, to the tube member using the joining member. Therefore, the sensor mechanism-equipped catheter with this construction is easy to produce.

The joining member may be formed from an insulating material, and seals, in an overall manner, at least a bonding wire extending from the sensor chip.

If the joining member is formed from an insulating material, short circuit of a bonding wire can be prevented, thereby reducing incidence of failures.

The joining member may be a hard member formed from a biologically compatible material.

The joining member is formed of a hard member, which results in a hard wall as a pressure barrier in a construction according to the second aspect of the invention. Thus, pressure escape in the direction toward the tube base end is more reliably prevented, so that more accurate pressure transmission to the pressure sensing device is achieved. The sensing precision thus further improves. Furthermore, use of the joining member formed from a biologically compatible material helps realize a sensor mechanism-equipped catheter that is highly compatible with human and animal bodies, and the like.

BRIEF DESCRIPTION OF THE DRAWINGS

The foregoing and further objects, features and advantages of the present invention will become apparent from the following description of preferred embodiments with reference to the accompanying drawings, wherein like numerals are used to represent like elements and wherein:

FIG. 3a is a longitudinal sectional view of a distal end portion the catheter;

FIG. 3b is a cross section taken on plane IIIb—IIIb of FIG. 3a;

FIG. 3c is a cross section taken on plane IIIc—IIIc of FIG. 3a;

FIG. 4a is a longitudinal sectional view of a catheter according to Modification 1;

FIG. 4b is a longitudinal sectional view of a catheter according to Modification 2;

FIG. 5a is a longitudinal sectional view of a catheter according to Modification 3;

FIG. 5b is a longitudinal sectional view of a catheter according to Modification 4;

FIG. 8a is a longitudinal sectional view of a distal end portion the catheter;

FIG. 8b is a cross section taken on plane VIIIb—VIIIb of FIG. 8a;

FIG. 8c is a cross section taken on plane VIIIc—VIIIc of FIG. 8a;

DETAILED DESCRIPTION OF PREFERRED EMBODIMENTS

Preferred embodiments of the present invention will be described in detail hereinafter with reference to the accompanying drawings.

A first embodiment wherein the invention is embodied in a blood vessel catheter having a sensor mechanism for detecting an obstacle will be described with reference to FIGS. 1–3.

A blood vessel catheter 1 (FIG. 3a) has a catheter tube (formed of polyvinylchloride and having a diameter of 1.6 mm in this embodiment) 2 insertable into a blood vessel, and an operating device provided on a base end portion of the catheter tube 2 for operating the catheter 1 from outside the body. The operating device is formed of, for example, a plurality of wires inserted in the catheter tube 2 and a wire operating device for operation of the wires. The base end portion of the catheter tube 2 is connected to a pressure pump for supplying an agent liquid, such as a contrast medium and the like, to a distal end portion of the catheter tube 2.

In the catheter 1 of this embodiment, a sensor assembly 3 has been formed separately from the catheter tube 2, and is connected to a distal end portion of the catheter tube 2.

Figure 1:
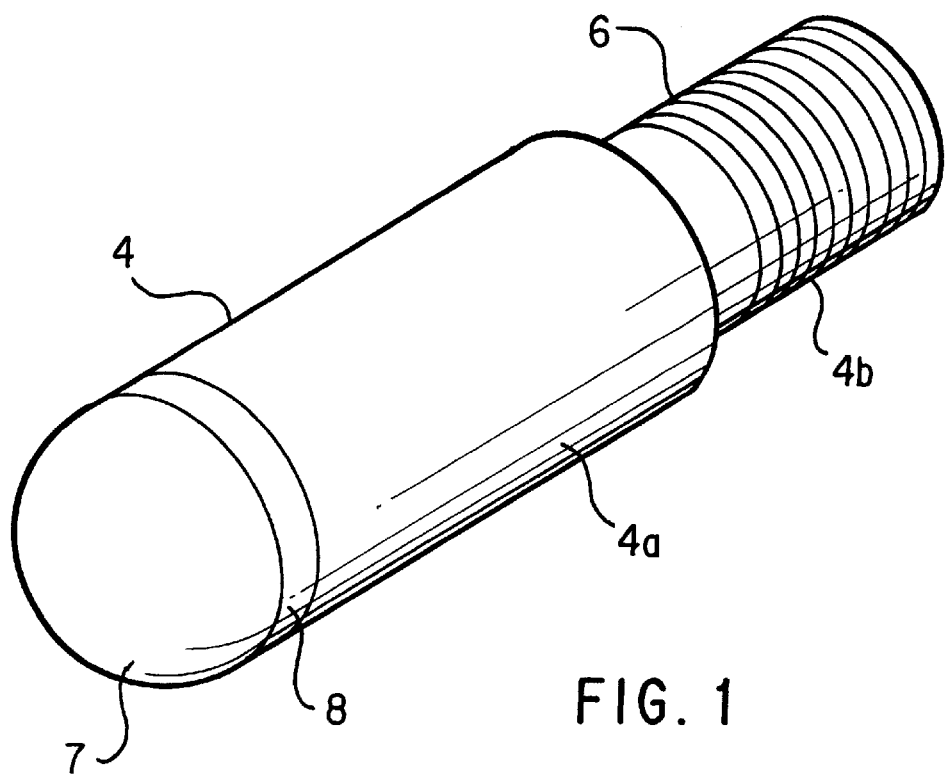
FIG. 1 is a perspective view of an outer tube and a piston that constitute a sensor assembly of a blood vessel catheter according to a first embodiment of the invention.
Figure 2:
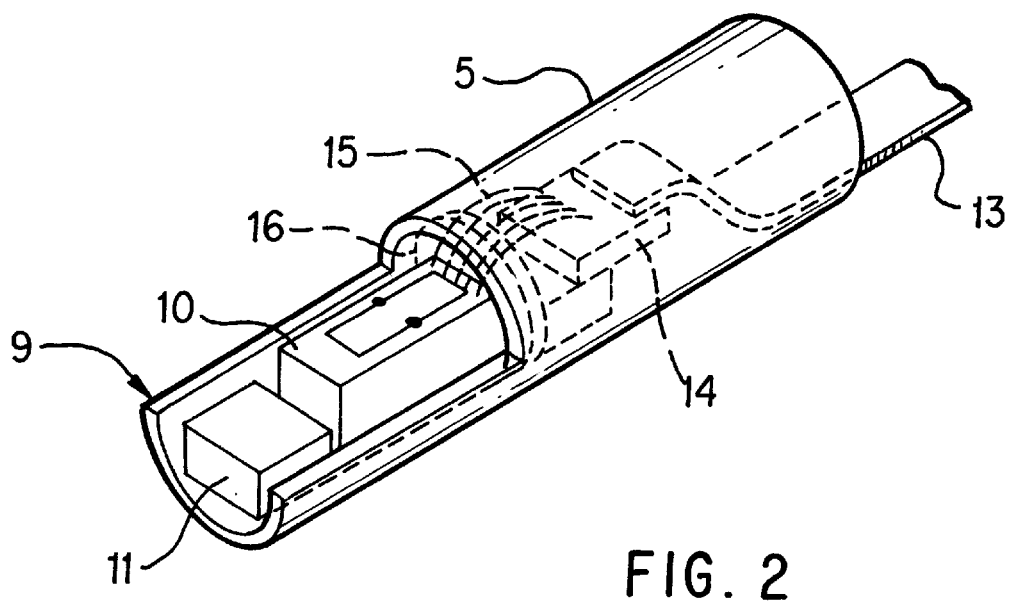
FIG. 2 is a perspective view of an inner tube, a seat member, a sensor chip and the like which constitute the sensor assembly shown in FIG. 1.

FIG. 1 shows an outer tube 4 constituting the sensor assembly 3. FIG. 2 shows an inner tube 5 constituting the sensor assembly 3. A distal end-side portion of the outer tube 4 forms a large-diameter portion 4a whose outside diameter substantially equals the outside diameter of the catheter tube 2, and a base end-side portion of the outer tube 4 forms a small-diameter portion 4b whose outside diameter is smaller than the outside diameter of the catheter tube 2. The small-diameter portion 4b is fitted into a distal end portion of the catheter tube 2. A plurality of slip-off preventative grooves 6 are formed on an outer peripheral surface of the small-diameter portion 4b, extending in circumferential directions. The outer tube 4 has a distal end opening to which a piston 7 is fitted in such a manner that the piston 7 is movable in directions of the length of the outer tube 4. The piston 7 forms a pressure-receiving portion. The junction between the piston 7 and the outer tube 4 is sealed by a seal member 8.

The inner tube 5 is a tubular member that has a smaller outside diameter and a shorter length than the outer tube 4. The inner tube 5 is fitted into the outer tube 4 in such a manner that the inner tube 5 is prevented from sliding. The inner tube 5 has a cut-out portion 9 that is formed in an end-side portion of the inner tube 5 that protrudes into the large-diameter portion 4a of the outer tube 4. A seat 11 carrying a semiconductor pressure sensor chip 10, that is, a pressure-sensing portion, is joined to an inner wall surface of the cut-out portion 9 by a joining member such as an epoxy resin or the like. A back pressure chamber 19 may be formed between an upper surface of the seat 11 and a lower surface of the sensor chip 10 as shown in FIG. 3a. The back pressure chamber 19 may be in communication with a relative pressure region through a back pressure hole (not shown) formed in the seat 11.

The semiconductor pressure sensor chip 10 has a thin wall portion in its central portion as shown in FIG. 3a. A distortion gage 12 is formed in an upper surface of the thin wall portion of the sensor chip 10. A bonding pad (not shown) formed on an upper surface of the sensor chip 10 is electrically connected to a relay tab 14 of a flat cable 13 by bonding wires 15. The flat cable 13 extends through the interior of the catheter tube 2 to a base end portion of the catheter tube 2.

A pressure barrier wall 16 is formed in the inner tube 5, at a location relatively toward the base end from the cut-out portion 9. The pressure barrier wall 16 seals the through bore of the inner tube 5 so that communication across the pressure barrier wall 16 is prevented. The pressure barrier wall 16 of this embodiment seals, in an overall manner, the bonding wires 15 extending from the sensor chip 10. Therefore, the pressure barrier wall 16 is formed from an insulating member. The pressure barrier wall 16 partially defines a medium-containing space 17 inside the outer tube 4. The medium-containing space 17 is filled with a silicone gel 18, that is, a pressure-transmitting medium. The pressure barrier wall 16 blocks flow of the silicone gel 18 in a direction toward the base end of the catheter tube 2.

It is desirable that components of the sensor assembly 3 that are externally exposed be formed from biologically compatible materials. In this embodiment, the outer tube 4 is formed from SUS 304, and the piston 7 is formed from polytetrafluorethylene (PTFE), and the seal member 8 is formed from a silicone resin. It is also desirable that an adhesive 20 adhering the joint portion of the sensor assembly 3 to the joint portion of the catheter tube 2 be made of a biologically compatible material such as a silicone resin.

Referring to FIGS. 3b and 3c, the catheter tube 2 has a partition wall 21 that extends in the direction of the axis of the catheter tube 2 and divides the interior of the catheter tube 2 into two regions. The two regions divided by the partition wall 21 are a signal line lumen 22 having a semi-circular sectional shape for housing the flat cable 13 and an agent liquid-supplying lumen 23 having a semi-circular sectional shape for supplying an agent liquid such as a contrast medium. The agent liquid-supplying lumen 23 has a hole 24 that extends through the wall of the catheter tube 2. Through the hole 24, the contrast medium or the like is supplied outside the catheter tube 2. The distal end-side opening of the agent liquid-supplying lumen 23 is closed by a seal plug 25.

The sensor assembly 3 is assembled, for example, in the following procedure. After the sensor chip 10 is mounted on the seat 11, the sensor chip 10 is wired-bonded to the flat cable 13. Subsequently, the flat cable 13 is inserted into the inner tube 5, and the seat 11 is fixed to the cut-out portion 9 using a joining member. After that, the pressure barrier wall 16 is formed in the inner tube 5 by, for example, disposing a fluidal insulating material and hardening the material. After the inner tube 5 is inserted into the outer tube 4 from the opening on the side of the small-diameter portion 4b, the silicone gel 18 is charged into the outer tube 4 from the opening on the side of the large-diameter portion 4a. The large-diameter portion-side opening is closed by the piston 7, and the junction portion between the piston 7 and the outer tube 4 is sealed by the seal member 8.

The sensor assembly 3 is mounted to a distal end portion of the catheter tube 2, which is of an existing type, as follows. The flat cable 13 is inserted into the signal line lumen 22 of the catheter tube 2. Subsequently, the sensor assembly 3 is fitted into the catheter tube 2 by inserting the small-diameter portion 4b of the outer tube 4, which constitutes the sensor assembly 3, from the distal end opening of the catheter tube 2. The junction between the catheter tube 2 and the outer tube 4 is adhered by the adhesive 20.

The sensing by the catheter 1 equipped with the sensor assembly 3 of this embodiment will now be described.

If the situation or condition ahead in the advancing direction of the catheter tube 2 changes, the tube insertion resistance changes and, therefore, the pressure acting on the piston 7 also changes. For example, if an obstacle (a blood clot or tumor) or a constricted site exists in a blood vessel in which the catheter tube 2 is inserted, a head portion of the sensor assembly 3 is pressed against the obstacle or constricted site so that the insertion resistance increases. The pressure acting on the piston 7 correspondingly increases. When such a pressure change occurs, the pressure of the silicone gel 18 contained in the medium-containing space 17 increases, so that the pressure that acts on the thin wall portion of the sensor chip 10 also increases. That is, a pressure change outside the sensor assembly 3 is transmitted indirectly to the sensor chip 10 by the silicone gel 18. In turn, the distortion of the thin wall portion of the sensor chip 10 increases, thereby causing a change in the resistance value of the distortion gage 12 formed on the thin wall portion. At this moment, the sensor chip 10 outputs an electrical signal indicating a pressure change. The electrical signal from the sensor chip 10 is inputted to and processed by an electrical circuit provided at the distal end of the catheter tube 2 so that the signal is visualized. Based on the visualized data, an operator is able to detect a condition in the advancing direction, that is, the presence of an obstacle, a constriction or the like, with an increased reliability. That is, if an obstacle or a constriction exists ahead of the catheter 1, the operator only needs to operate the wires to direct the head portion of the sensor assembly 3 in such a direction that the pressure decreases, while monitoring the visualized data. The use of the sensor assembly 3 is not limited to the sensing of an obstacle, a constriction and the like. The sensor assembly 3 may also be used for other purposes, for example, to measure blood pressure. If angiography is to be performed to detect the position of the sensor assembly 3 in a vessel in a more detailed manner, a contrast medium is supplied into the agent liquid-supplying lumen 23 and ejected from the hole 24. It is also possible to supply a liquid other than a contrast medium, for example, a medical agent such as a fibrinolytic agent or the like. Further, it is also possible to collect a blood sample or the like, through the agent liquid-supplying lumen 23.

Major advantages of this embodiment will be stated below.

(a) The embodiment enables an operator to guide the leading end of the catheter tube 2 to a desired site in a blood vessel. Furthermore, since the sensor chip 10 and the like are mounted in the cut-out portion 9 formed in an end-side portion of the inner tube 5, and the inner tube 5 is then fitted into the outer tube 4, it is possible to dispose the sensor chip 10 at a desired position in the sensor assembly 3. Thus, the catheter 1 of the embodiment is easy to produce.

(b) A desired catheter can be produced simply by attaching the sensor assembly 3, provided as a separate unit, to a distal end portion of the catheter tube 2. Unlike the conventional catheters, wherein the individual components of the sensor portion are directly mounted in a catheter tube, the catheter tube 2 of the embodiment can easily be produced.

(c) In this embodiment, the slip-off preventative grooves 6 are formed on the outer peripheral surface of the small-diameter portion 4b of the outer tube 4, thereby forming an irregular surface for securing to the catheter tube 2. Therefore, the resistance on the joint interface between the outer tube 4 and the catheter tube 2 is increased, so that the sensor assembly 3 is substantially prevented from slipping off from the catheter tube 2. Furthermore, since the joint portion of the outer tube 4 has a small diameter, a step is not formed at the junction when the sensor assembly 3 is fitted into the catheter tube 2. With the flush outer peripheral surfaces of the catheter tube 2 and the sensor assembly 3, the catheter 1 is unlikely to inconveniently engage with a blood vessel wall or the like when inserted thereinto. The catheter 1 of the embodiment thus provides good operability.

(d) In the catheter 1 of the embodiment, the components of the sensor assembly 3 that are externally exposed, that is, the outer tube 4, the piston 7 and the seal member 8, are formed from biologically compatible materials. Therefore, contact of the sensor assembly 3 with biological substances, such as various substances in blood, will not cause blood clotting or other undesired biological reactions. Therefore, the catheter 1 of the embodiment is highly compatible with human and animal bodies, and the like, and is suitable for use in vivo.

(e) In the catheter 1 of the embodiment, the sensor assembly 3 and the catheter tube 2 are adhered by the adhesive 20 made of a biologically compatible material. Therefore, reliable prevention of the sensor assembly 3 from slipping off from the catheter tube 2 is ensured and, at the same time, biological compatibility is improved. Thus, the catheter 1 is highly suitable for use in vivo.

(f) In the catheter 1 of the embodiment, the semiconductor pressure sensor chip 10 of a very small size is used as a pressure-sensing portion. Therefore, compared with cases where other pressure sensing devices or methods are employed, the embodiment allows a considerable size reduction of the sensor assembly 3 and, therefore, makes a highly practical catheter.

(g) With provision of the pressure barrier wall 16, the catheter 1 of the embodiment prevents the silicon gel 18 from flowing toward the base end of the catheter tube 2. Therefore, the difference between an increase in the pressure acting on the thin wall portion of the sensor chip 10 and the corresponding increase in the pressure of the silicon gel 18 is reduced, so that accurate pressure transmission is achieved. The precision in the sensing by the sensor assembly 3 therefore improves. The pressure barrier wall 16 also achieves an advantage of facilitating the process of charging the silicon gel 18 into the medium-containing space 17.

The invention is not limited to the embodiment described above, but may be modified as follows.

(1) FIG. 4a shows Modification 1, wherein a sensor assembly 31 has been produced as a separate unit. The sensor assembly 31 is produced by fitting an inner tube 33 carrying a sensor chip 10 and the like, into an outer tube 32 whose diameter is substantially consistent over its entire length. The outside diameter of the outer tube 32 substantially equals the inside diameter of a catheter tube 2. The sensor assembly 31 is fitted into the catheter tube 2 in such a manner that the sensor assembly 31 is mostly disposed inside the catheter tube 2 but only the piston 7 is externally exposed. A plurality of slip-off preventative grooves 6 are formed on an outer peripheral surface of a base end-side portion of the outer tube 32, extending in circumferential directions. That is, the joint portion of the outer tube 32 to the catheter tube 2 has an irregular surface. This construction also enables a desired catheter to be produced simply by attaching the sensor assembly 31 to a distal end portion of an existing catheter tube.

(2) FIG. 4b shows Modification 2, wherein a sensor assembly 41 employs a joining member 43 formed by loading a fluidal seal material, such as epoxy resin or the like, and then hardening the seal material, in order to fix a seat 11 to a cut-out portion 9. The joining member 43 seals the through bore of an inner tube 5 so that communication across the joining member 43 is prevented. That is, the joining member 43 also serves as a pressure barrier wall 43a. This construction also enables a desired catheter to be produced simply by attaching the sensor assembly 41 to a distal end portion of an existing catheter tube.

(3) FIG. 5a shows Modification 3, wherein a sensor assembly 51 has been produced as a separate unit. The sensor assembly 51 is produced by fitting only a portion of an inner tube 5 carrying a sensor chip 10 and the like, into an outer tube 52 whose diameter is substantially consistent over its entire length and substantially equals the diameter of a catheter tube 2. For fitting into a catheter tube 2, the inner tube 5 protrudes from the outer tube 52. A plurality of slip-off preventative grooves 6 are formed on an outer peripheral surface of a joint portion of the inner tube 5 to the catheter tube 2, extending in circumferential directions. That is, the joint portion of the inner tube 5 to the catheter tube 2 has an irregular surface. This construction also enables a desired catheter to be produced simply by attaching the sensor assembly 51 to a distal end portion of an existing catheter tube.

(4) FIG. 5b shows Modification 4, wherein a sensor assembly 61 has been produced as a separate unit. The sensor assembly 31 has an outer tube 62 whose diameter is substantially consistent over its entire length and is larger than the diameter of a catheter tube 2. An inner tube 63 that caries a sensor chip 10 and the like, is fitted into and disposed completely inside the outer tuber 62. The outside diameter of the inner tube 63 substantially equals the outside diameter of the catheter tube 2. A distal end portion of the catheter tube 2 is fitted into a base end-side opening of the outer tube 62. In Modification 4, a plurality of slip-off preventative grooves 6 are formed in an inner peripheral surface of a base end-side portion of the outer tube 62.

(5) It is also possible to replace the silicon gel 18 with a gel material other than silicone, as a pressure-transmitting medium. Further, a material having a fluidity, such as a silicone oil, may also be used. Considering that so-called "dancing" phenomenon is unlikely to occur in the pressure-transmitting medium, it is preferred to employ a gel material such as the silicone gel 18.

(6) It is also possible to form an irregular joint surface in the form other than the slip-off preventative grooves 6. For example, protuberances and the like may instead be formed.

A second embodiment wherein the invention is embodied in a catheter equipped with a sensor mechanism for detecting an obstacle will now be described with reference to FIGS. 6 and 8. The second embodiment is based on Modification 2 shown in FIG. 4b.

Figure 6:
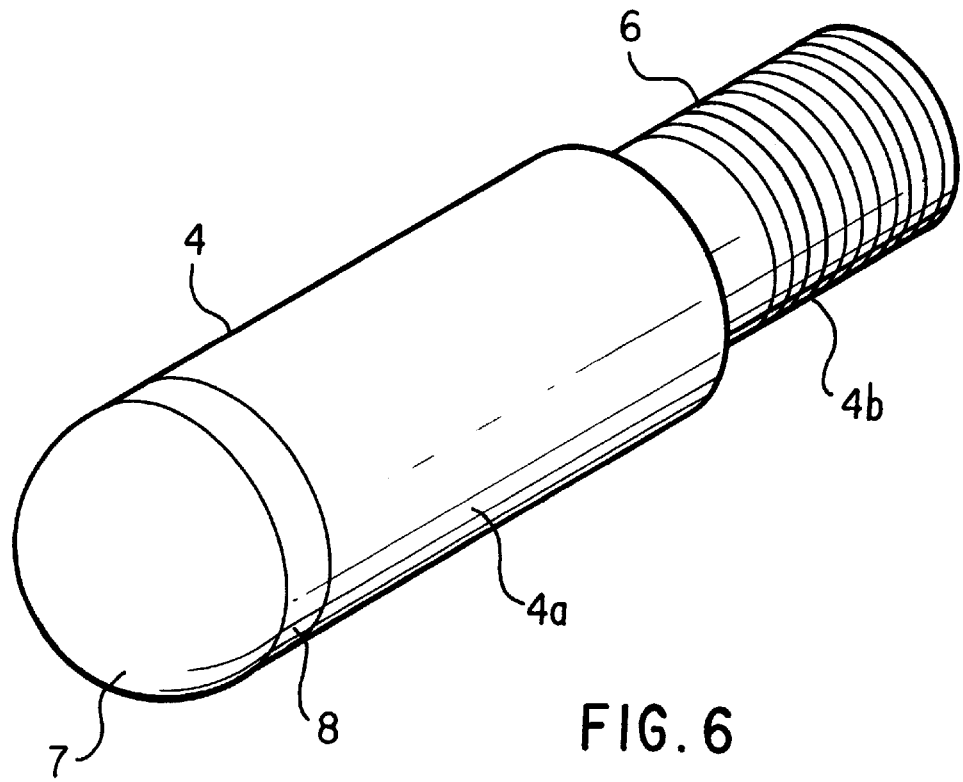
FIG. 6 is a perspective view of an outer tube and a piston that constitute a sensor assembly of a blood vessel catheter according to a second embodiment of the invention.
Figure 7:
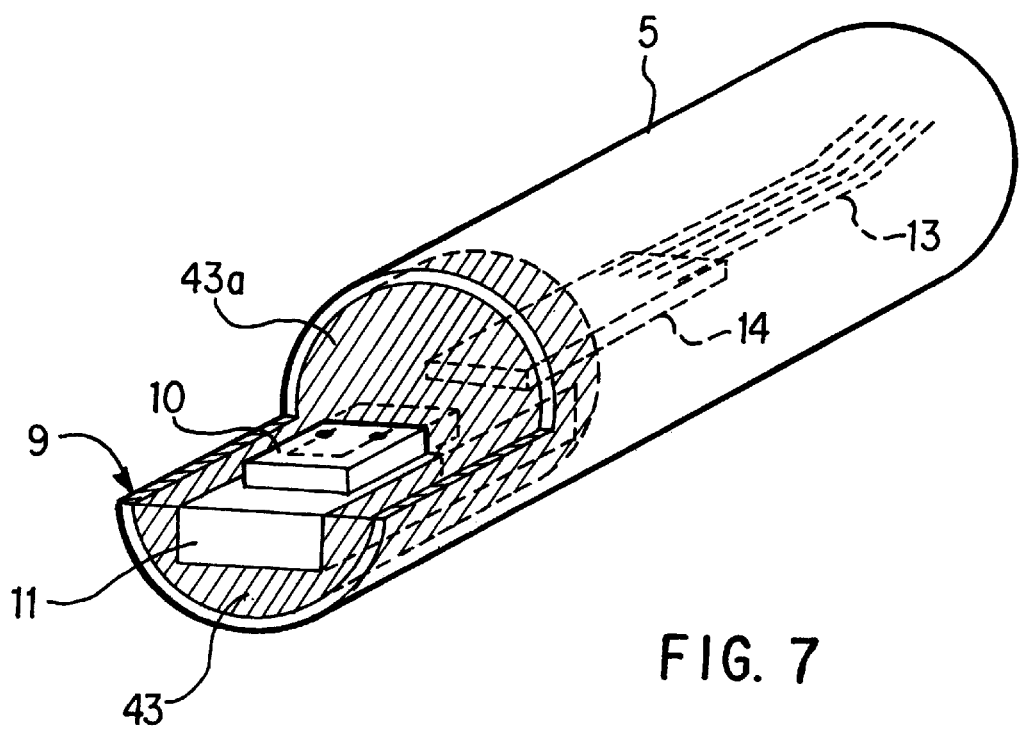
FIG. 7 is a perspective view of an inner tube, a seat member, a sensor chip and the like which constitute the sensor assembly shown in FIG. 6.

FIG. 6 shows an outer tube 4 constituting a sensor assembly 41. FIG. 2 shows an inner tube 5 constituting the sensor assembly 41. A distal end-side portion of the outer tube 4 forms a large-diameter portion 4a whose outside diameter substantially equals the outside diameter of the catheter tube 2. A base end-side portion of the outer tube 4 forms a smal-diameter portion 4b whose outside diameter is smaller than the outside diameter of the catheter tube 2. The small-diameter portion 4b is fitted into a distal end portion of the catheter tube 2. A plurality of slip-off preventative grooves 6 are formed on an outer peripheral surface of the small-diameter portion 4b, extending in circumferential directions. The outer tube 4 has a distal end opening to which a piston 7 is fitted in such a manner that the piston 7 is movable in directions of the length of the outer tube 4. The piston 7 forms a pressure-receiving portion. The junction between the piston 7 and the outer tube 4 is sealed by a seal member 8.

The inner tube 5 is a tubular member that has a smaller outside diameter and a shorter length than the outer tube 4. The inner tube 5 is fitted into the outer tube 4 in such a manner that the inner tube 5 is prevented from sliding. The inner tube 5 has a cut-out portion 9 that is formed in an end-side portion of the inner tube 5 that protrudes into the large-diameter portion 4a of the outer tube 4. A seat 11 carrying a semiconductor pressure sensor chip 10, that is, a pressure sensitive device, is joined to an inner wall surface of the cut-out portion 9 by a joining member 43. A back pressure chamber 19 may be formed between an upper surface of the seat 11 and a lower surface of the sensor chip 10 as shown in FIG. 8a. The joining member 43 is formed by hardening a fluidal material.

It is most desirable that the joining member 43 satisfy all of the following three conditions: (a) being formed from an insulating material, (b) being hard, and (c) being formed from a biologically compatible material. Considering these conditions, this embodiment employs a thermosetting resin such as epoxy resin. Epoxy resin satisfies all the three conditions. It is also possible to use a resin other than epoxy resin, such as silicone resin, polyurethane resin or the like. Further, a photo-setting resin may also be used.

A back pressure chamber 19 may be formed between an upper surface of the seat 11 and a lower surface of the sensor chip 10 as shown in FIG. 8a. The back pressure chamber 19 may be in communication with a relative pressure region through a back pressure hole (not shown) formed in the seat 11.

The semiconductor pressure sensor chip 10 has a thin wall portion in its central portion as shown in FIG. 8a. A distortion gage 12 is formed in an upper surface of the thin wall portion of the sensor chip 10. A bonding pad (not shown) formed on an upper surface of the sensor chip 10 is electrically connected to a relay tab 14 of a flat cable 13 by bonding wires 15. The flat cable 13 extends through the interior of the catheter tube 2 to a base end portion of the catheter tube 2.

The joining member 43 seals the gaps between a lower surface and a side surface of the seat 11 and an inner peripheral surface of the cut-out portion 9 of the inner tube 5 and, further, extends, in a wrapping manner, over base end-side portions of the seat 11 and the sensor chip 10, thereby sealing the through bore of the inner tube 5 so that communication through the inner tube 5 is prevented. The joining member 43 thus forms a pressure barrier wall 43a in the inner tube 5, at a location slightly toward the base end from the cut-out portion 9. The pressure barrier wall 43a seals the entire bonding wires 15 extending from the sensor chip 10. The pressure barrier wall 43a partially defines a medium-containing space 17 inside the outer tube 4. The medium-containing space 17 is filled with a silicone gel 18, that is, a pressure-transmitting medium. The pressure barrier wall 43a blocks flow of the silicone gel 18 in a direction toward the base end of the catheter tube 2.

It is desirable that components of the sensor assembly 41 that are externally exposed be formed from biologically compatible materials. In this embodiment, the outer tube 4 is formed from SUS 304, and the piston 7 is formed from polytetrafluorethylene (PTFE), and the seal member 8 is formed from a silicone resin. It is also desirable that an adhesive 20 adhering the joint portion of the sensor assembly 41 to the joint portion of the catheter tube 2 be made of a biologically compatible material such as a silicone resin.

Referring to FIGS. 8b and 8c, the catheter tube 2 has a partition wall 21 that extends in the direction of the axis of the catheter tube 2 and divides the interior of the catheter tube 2 into two regions. The two regions divided by the partition wall 21 are a signal line lumen 22 having a semi-circular sectional shape for housing the flat cable 13 and an agent liquid-supplying lumen 23 having a semi-circular sectional shape for supplying an agent liquid such as a contrast medium. The agent liquid-supplying lumen 23 has a hole 24 that extends through the wall of the catheter tube 2. Through the hole 24, the contrast medium or the like is supplied outside the catheter tube 2. The distal end-side opening of the agent liquid-supplying lumen 23 is closed by a seal plug 25.

The sensor assembly 41 is assembled, for example, in the following procedure. After the sensor chip 10 is mounted on the seat 11, the sensor chip 10 is wired-bonded to the flat cable 13. Subsequently, the flat cable 13 is inserted into the inner tube 5. After the seat 11 is disposed in the cut-out portion 9 using the joining member 43, a fluidal material of the joining member 43 is loaded at a predetermined site in the cut-out portion 9 of the inner tube 5, and then hardened by heat from a heater of the like. As a result, the seat 11 and the sensor chip 10 are fixed to an inner peripheral surface of the cut-out portion 9 by the joining member 43, and the pressure barrier wall 43a is formed at a position slightly toward the base end from the cut-out portion 9.

After the inner tube 5 is inserted into the outer tube 4 from the opening on the side of the small-diameter portion 4b, the silicone gel 18 is charged into the outer tube 4 from the opening on the side of the large-diameter portion 4a. The large-diameter portion-side opening is closed by the piston 7, and the junction portion between the piston 7 and the outer tube 4 is sealed by the seal member 8.

The sensor assembly 41 is mounted to a distal end portion of the catheter tube 2, which is of an existing type, as follows. The flat cable 13 is inserted into the signal line lumen 22 of the catheter tube 2. Subsequently, the sensor assembly 41 is fitted into the catheter tube 2 by inserting the small-diameter portion 4b of the outer tube 4, which constitutes the sensor assembly 41, from the distal end opening of the catheter tube 2. The junction between the catheter tube 2 and the outer tube 4 is adhered by the adhesive 20.

The sensing by the catheter 1 equipped with the sensor assembly 41 of this embodiment will now be described.

If the situation or condition ahead in the advancing direction of the catheter tube 2 changes, the tube insertion resistance changes and, therefore, the pressure acting on the piston 7 also changes. For example, if an obstacle (a blood clot or tumor) or a constricted site exists in a blood vessel in which the catheter tube 2 is inserted, a head portion of the sensor assembly 41 is pressed against the obstacle or constricted site so that the insertion resistance increases. The pressure acting on the piston 7 correspondingly increases. When such a pressure change occurs, the pressure of the silicone gel 18 contained in the medium-containing space 17 increases, so that the pressure that acts on the thin wall portion of the sensor chip 10 also increases. That is, a pressure change outside the sensor assembly 41 is transmitted indirectly to the sensor chip 10 by the silicone gel 18. In turn, the distortion of the thin wall portion of the sensor chip 10 increases, thereby causing a change in the resistance value of the distortion gage 12 formed on the thin wall portion. At this moment, the sensor chip 10 outputs an electrical signal indicating a pressure change. The electrical signal from the sensor chip 10 is inputted to and processed by an electrical circuit provided at the distal end of the catheter tube 2 so that the signal is visualized. Based on the visualized data, an operator is able to detect a condition in the advancing direction, that is, the presence of an obstacle, a constriction or the like, with an increased reliability. That is, if an obstacle or a constriction exists ahead of the catheter 1, the operator only needs to operate the wires to direct the head portion of the sensor assembly 41 in such a direction that the pressure decreases, while monitoring the visualized data. The use of the sensor assembly 41 is not limited to the sensing of an obstacle, a constriction and the like. The sensor assembly 41 may also be used for other purposes, for example, to measure blood pressure. If angiography is to be performed to detect the position of the sensor assembly 41 in a vessel in a more detailed manner, a contrast medium is supplied into the agent liquid-supplying lumen 23 and ejected from the hole 24. It is also possible to supply a liquid other than a contrast medium, for example, a medical agent such as a fibrinolytic agent or the like. Further, it is also possible to collect a blood sample or the like, through the agent liquid-supplying lumen 23.

Major advantages of this embodiment will be stated below.

(a) The embodiment enables an operator to guide the leading end of the catheter tube 2 to a desired site in a blood vessel. Furthermore, a portion of the joining member 43 formed by loading a fluidal material and hardening the material also serves as the pressure barrier wall 43a. Therefore, the joining member 43 (pressure barrier wall 43a) reliably seals an interior portion of the catheter tube 2, even if it has a small diameter, without allowing a gap to form, in comparison with a conventional solid pressure barrier wall. Thus, this construction contributes to diameter reduction of the catheter 1. Since the thus-formed pressure barrier wall 43a blocks flow of the silicon gel 18 in the direction toward the base end of the catheter tube 2, pressure escape in that direction is prevented. Therefore, the difference between an increase in the pressure acting on the piston 7, that is, a pressure-receiving portion, and the corresponding increase in the pressure of the silicon gel 18 is reduced, so that an accurate pressure can be transmitted to the sensor chip 10, that is, a pressure sensing device. The sensing precision thereby improves.

(b) Since the joining member 43 carries the pressure barrier wall 43a as a portion thereof, the number of component parts is correspondingly reduced, thereby leading to a cost reduction.

(c) In the catheter 1 of this embodiment, the sensor assembly including the inner tube 5, the outer tube 4 and the like, is formed as a separate member. Therefore, a desired catheter can be formed simply by fitting the sensor assembly 41 to a distal end portion of an existing catheter tube 2. Unlike a conventional catheters in which the individual components of a sensor portion are directly mounted in the catheter tube, the catheter 1 is easy to produce.

(d) In this embodiment, the semiconductor pressure sensor chip 10 of a very small size is used as a pressure sensing device. Therefore, the sensor assembly 41 can be reduced in diameter, compared with cases where the pressure sensing device is constructed in other manners. The construction employing a semiconductor pressure sensor chip is also more practical. Furthermore, with the cut-out portion 9 formed at a distal end side of the inner tube 5, it becomes relatively easy to fix the seat 11, which carries the sensor chip 10, to the inner tube 5 using the joining member 43. Therefore, the catheter 1 is easy to produce.

(e) The joining member 43 used in the catheter 1 is formed from an epoxy resin that has a good insulating characteristic. The bonding wires 15 are entirely sealed by the joining member 43. Therefore, short circuit of a bonding wire can be prevented, thereby reducing failure incidence. Therefore, the catheter 1 is suitable for use in vivo.

(f) Since the joining member 43 employed in the catheter 1 is formed from an epoxy resin, which is normally harder than other resins, the pressure barrier wall 43a is also hard. Therefore, the pressure barrier wall 43a does not substantially deform, upon receiving pressure. As a result, pressure escape in the direction toward the base end of the catheter tube 2 is more reliably prevented, so that more accurate pressure transmission to the sensor chip 10 is achieved. The sensing precision thus further improves. Furthermore, use of the joining member 43 formed from a biologically compatible material helps realize a catheter that is highly compatible with human and animal bodies, and the like. Thus, the catheter 1 is suitable for use in vivo.

(g) In the catheter 1 of the embodiment, the components of the sensor assembly 41 that are externally exposed, that is, the outer tube 4, the piston 7 and the seal member 8, are formed from biologically compatible materials. Therefore, contact of the sensor assembly 41 with biological substances, such as various substances in blood, will not cause blood clotting or other undesired biological reactions. Therefore, the catheter 1 of the embodiment is highly compatible with human and animal bodies, and the like, and is suitable for use in vivo.

The present invention is not limited to the embodiment described above, but may be modified as follows.

Figure 9A:
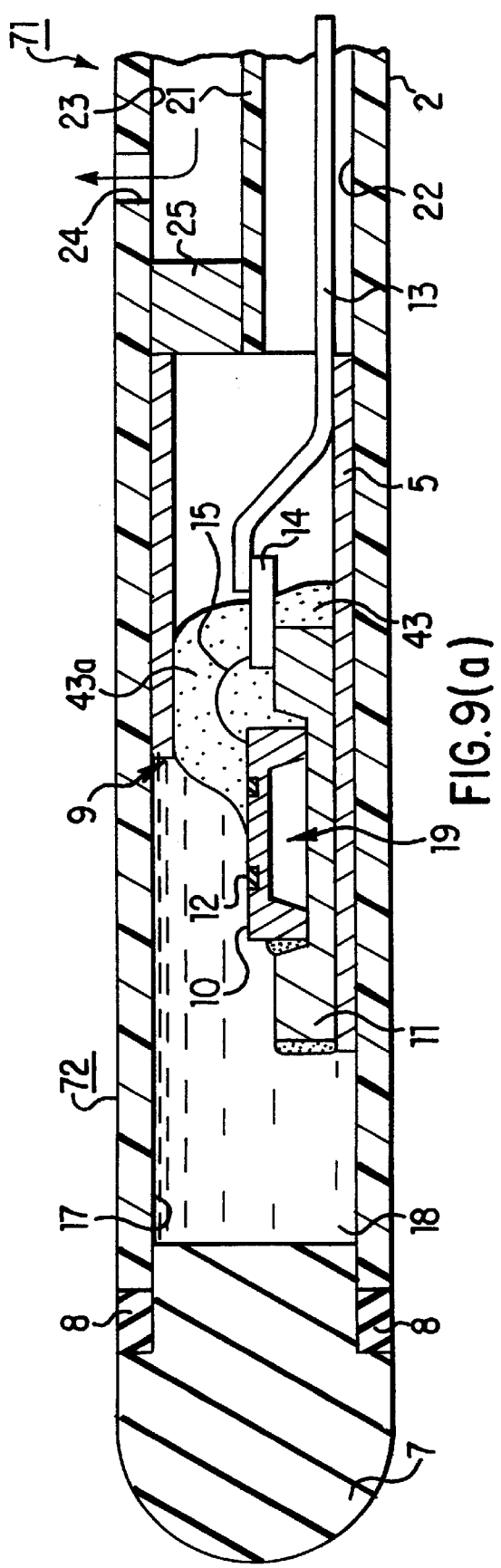
FIG. 9a is a longitudinal sectional view of a catheter according to Modification 5.
Figure 9B:
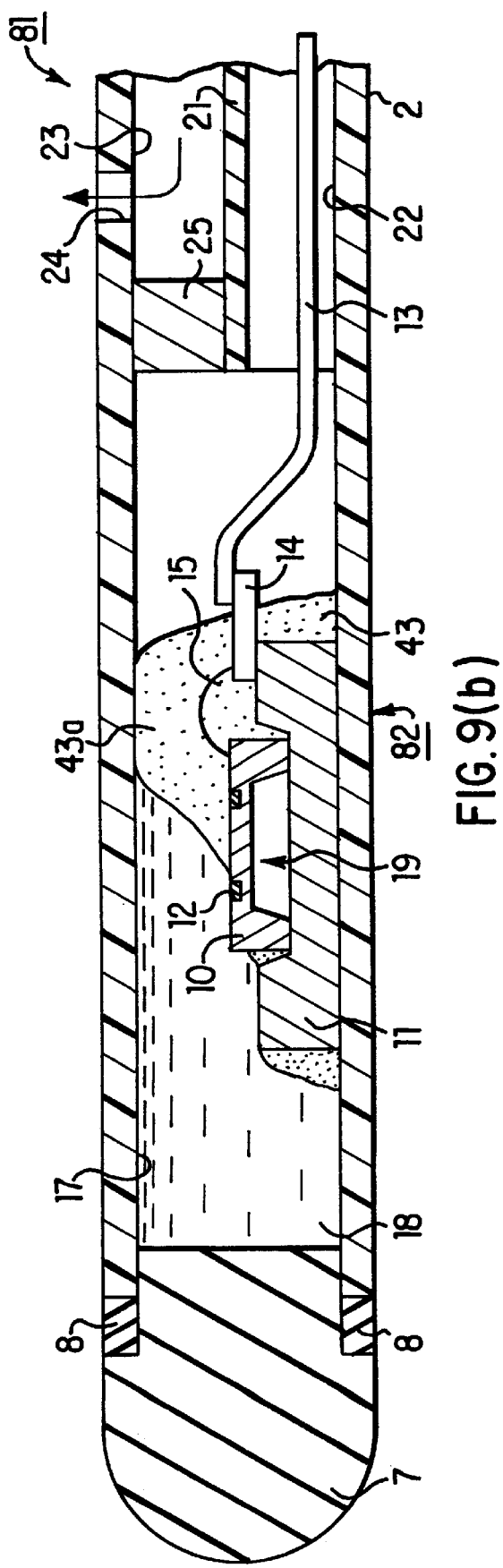
FIG. 9b is a longitudinal sectional view of a catheter according to Modification 6.
Figure 10:
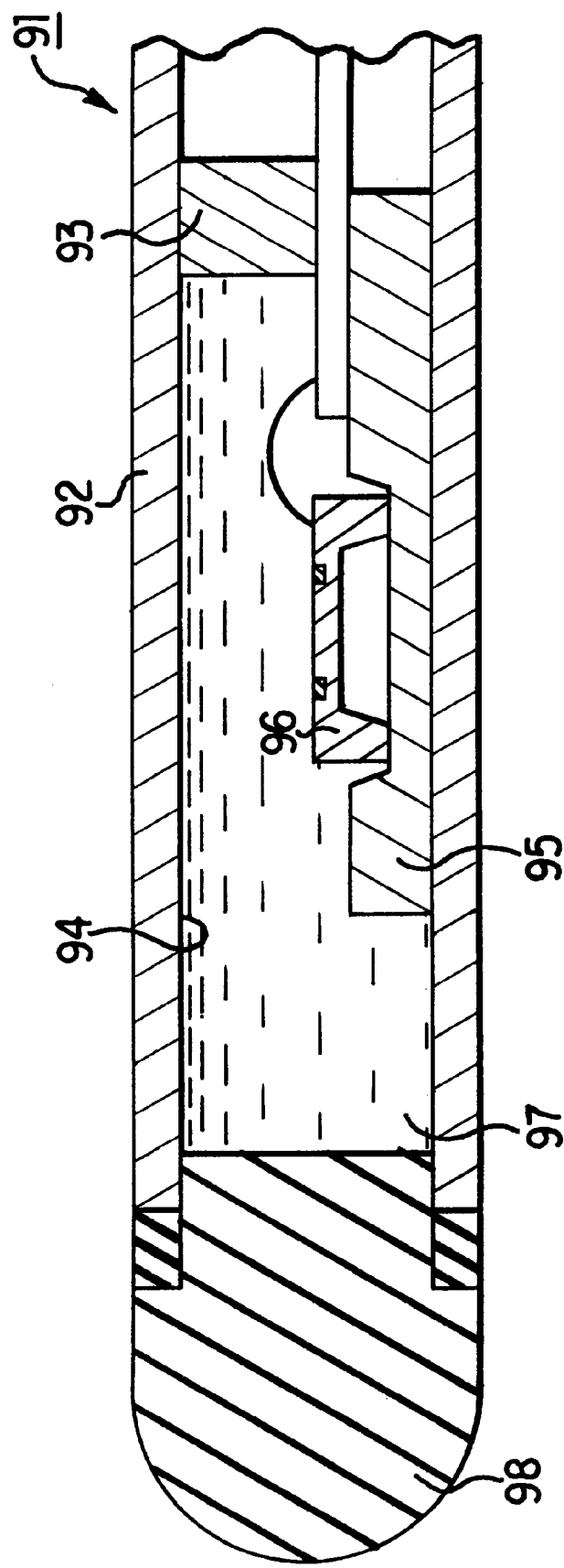
FIG. 10 illustrates a related art catheter.

(1) FIG. 9a shows Modification 5, wherein a sensor assembly 72 of a catheter 71 has a construction similar to a construction wherein the outer tube 4 is omitted from the sensor assembly 41 of the second embodiment. An inner tube 72 constituting the sensor assembly 72 is fitted into and disposed completely inside an existing catheter tube 2. A joining member 43 substantially the same as in the second embodiment is provided in the inner tube 5 and forms a pressure barrier wall 43a. A distal end opening of the catheter tube 2 is closed by a piston 7. This construction also provides a sensor mechanism-equipped catheter that achieves a high sensing precision and that is suitable for a diameter reduction. Furthermore, omission of the outer tube 4 correspondingly simplifies the construction, and allows a further reduction of the catheter 71 in diameter.

(2) FIG. 4(b) shows Modification 6, wherein a sensor portion 82 of a catheter 81 is formed without employing a tube member. That is, a seat 11 and a sensor chip 10 are disposed directly in an existing catheter tube 2. A joint member 43 substantially the same as in the second embodiment and Modification 5 is provided inside the catheter tube 2 and forms a pressure barrier wall 43a. This construction also provides a sensor mechanism-equipped catheter that achieves a high sensing precision and that is suitable for a diameter reduction to some extent.

(3) The joining member 43 does not need to satisfy all of the following three conditions: (a) being formed from an insulating material, (b) being hard, and (c) being formed from a biologically compatible material. It is possible to use a joining member that satisfies two of the conditions, that is, the conditions (a) and (b), or the conditions (b) and (c), or the conditions (c) and (a). Furthermore, a joining member that satisfies only one of the conditions, that is, only the condition (a), or only the condition (b), or only the condition (c), can be used satisfactorily to some extent.

(4) It is also possible to replace the silicon gel 18 with a gel material other than silicone, as a pressure-transmitting medium. Further, a material having a fluidity, such as a silicone oil, may also be used. Considering that so-called "dancing" phenomenon is unlikely to occur in the pressure-transmitting medium, it is preferred to employ a gel material such as the silicone gel 18.

(5) It is also possible to form an irregular joint surface in the form other than the slip-off preventative grooves 6. For example, protuberances and the like may instead be formed.

Besides the constructions characteristic to the invention, various additional constructions disclosed in the foregoing embodiments and modifications will be listed below, together with their advantages.

(1) A sensor mechanism-equipped catheter according to the first aspect of the invention may have a construction wherein the catheter tube has a plurality of lumens divided by a member extending in the direction of the axis of the catheter tube, and wherein at least one of the lumens is a liquid-passing lumen that has a through hole that extends through a wall of the catheter tube. This construction makes it possible to supply a liquid, such as a contrast medium or other medical agent, to a distal end portion of the catheter tube.

(2) In a sensor mechanism-equipped catheter according to the foregoing construction (1), the liquid-passing lumen may be designed to supply a medical agent liquid to the outside of the catheter tube through the through hole. This construction makes it possible to perform a curing operation by supplying a medical agent to a distal end portion of the catheter.

(3) In a sensor mechanism-equipped catheter according to the first aspect of the invention, or the construction (1) or (2), the sensor portion and the catheter tube may have substantially the same outside diameter. This construction eliminates a step at the junction between the sensor portion and the catheter tube and, therefore, reduces the incidence of inconvenient engagement of the catheter with a blood vessel or the like when the catheter is inserted thereinto, thereby improving operability.

(4) A sensor mechanism-equipped catheter according to the second aspect of the invention, may have a construction wherein the joining member is formed from an epoxy resin. With this construction, the sensor mechanism-equipped catheter achieves a high sensing precision, and is suitable for a diameter reduction, easy to produce, robust against failures, and suitable for use in vivo.

(5) A sensor mechanism-equipped catheter according to the second aspect of the invention may have a construction wherein the tube member is fitted into and disposed completely inside the catheter tube. Thereby, it becomes possible to simplify the construction of the sensor mechanism-equipped catheter and to further reduce the catheter in diameter.

(6) A sensor assembly for a catheter for detecting a pressure change may include a pressure-receiving portion, a pressure-transmitting medium and a pressure sensing device. The sensor assembly may be disposed at a distal end side of the catheter tube. The sensor portion is provided separately from the catheter tube, and further includes a tube member fitted to a distal end portion of the catheter tube. A joining member is provided inside the tube member and fixes the pressure sensing device. The joining member is formed by loading a fluidal seal material and hardening the material. The joining member also serves as a pressure barrier wall that blocks flow of the pressure-transmitting medium toward a base end of the catheter tube. If this sensor assembly is employed, it becomes possible to produce a sensor mechanism-equipped catheter according to the invention, with a high reliability.

The "biologically compatible material" used in the above description is defined as a material that has a low reactivity with various biological substances, including substances in blood, lymph and body fluid. Examples of the biologically compatible material include, but not limited to, resins such as silicone resin, polyvinylchloride and the like, metals such as gold, stainless steel and the like, ceramics such as alumina, zirconia and the like.

As is apparent from the above description, the sensor mechanism-equipped catheter according to the first aspect of the invention is easy to produce since the pressure-sensing portion can be disposed at a desired position.

Furthermore, if a sensor portion is provided as a separate member, it become easier to produce a sensor mechanism-equipped catheter, in comparison with the conventional art, wherein the individual components of a sensor portion are directly mounted in a catheter tube.

If an irregular joint surface is provided at the interface between the sensor portion and the catheter tube, the sensor portion is substantially prevented from slipping off from the catheter tube. Therefore, the sensor mechanism-equipped catheter becomes suitable for use in vivo.

If a plurality of slip-off preventative grooves are formed on a joint portion of a tube member to the catheter, reliable prevention of the sensor portion from slipping off from the catheter is ensured. Therefore, the sensor mechanism-equipped catheter is suitable for use in vivo, and reduces the incidence of inconvenient engagement with a blood vessel wall or the like when the catheter is inserted thereinto, thereby improving operability.

If a component of the sensor portion that is external exposed is formed from a biologically compatible material, the compatibility with human and animal bodies and the like improves, so that the sensor mechanism-equipped catheter becomes more suitable for use in vivo.

If the catheter tube and the sensor portion are adhered by an adhesive made of a biologically compatible material, reliable prevention of the sensor portion from slipping off from the catheter tube is ensured and, at the same time, the compatibility with human and animal bodies and the like improves. Therefore the sensor mechanism-equipped catheter becomes more suitable for use in vivo.

The sensor mechanism-equipped catheter according to the second aspect of the invention achieves a high sensing precision, and is suitable for a diameter reduction. Furthermore, the number of component parts is reduced, leading to a cost reduction.

If a sensor portion is provided as a separate member, it become easier to produce a sensor mechanism-equipped catheter, in comparison with the conventional art, wherein the individual components of a sensor portion are directly mounted in a catheter tube.

If a semiconductor pressure sensor chip is employed as a pressure sensing device, a further diameter reduction and improvements in practicability can be achieved. Furthermore, it becomes easier to produce a sensor mechanism-equipped catheter.

If the joining member is from of an insulating material and seals, in an overall manner, the wire bonding extending from the sensor chip, the sensor mechanism-equipped catheter becomes robust against failures and, therefore, suitable for use in vivo.

If the joining member, serving also as a pressure barrier wall, is a hard member formed from a biologically compatible material, the sensing precision further improves and, at the same time, a high compatibility with human and animal bodies and the like is achieved, so that the sensor mechanism-equipped catheter becomes more suitable for use in vivo.

While the present invention has been described with reference to what are presently considered to be preferred embodiments thereof, it is to be understood that the invention is not limited to the disclosed embodiments, modifications or constructions. To the contrary, the invention is intended to cover various modifications and equivalent arrangements included within the spirit and scope of the appended claims.

What is claimed is:

1. A sensor mechanism-equipped catheter comprising:
   a catheter tube; and
   a sensor portion including a pressure-receiving portion disposed at a distal end of the catheter tube, a pressure-sensing portion, an outer tube holding the pressure-receiving portion at a distal end side of the outer tube, and an inner tube supporting the pressure-sensing portion at an end side of the inner tube, the inner tube being fitted into the outer tube, the sensor portion further including, a pressure-transmitting medium that fills a space between the pressure-receiving portion and the pressure-sensing portion, the space being formed within the outer tube, and a pressure barrier wall that prevents the pressure-transmitting medium from flowing toward the catheter tube,
   wherein the sensor portion is provided as a unit separate from the catheter tube and is mounted at the distal end of the catheter tube, and at least one of the outer tube and inner tube has an irregular surface that is formed in a joint portion thereof fittable to the distal end of the catheter tube.

2. A sensor mechanism-equipped catheter according to claim 1, wherein the sensor portion is provided as a unit separate from the catheter tube and is mounted at the distal end side of the catheter tube.

3. A sensor mechanism-equipped catheter according to claim 2, wherein at least one of the outer tube and the inner tube has an irregular surface that is formed in a joint portion thereof fittable to the distal end side of the catheter tube.

4. A sensor mechanism-equipped catheter according to claim 1, wherein the joint portion is formed as a base end-side small-diameter portion of the outer tube, and wherein a plurality of slip-off preventative grooves extend, in a circumferential direction, on an outer peripheral surface of the small-diameter portion.

5. A sensor mechanism-equipped catheter according to claim 1, wherein a biologically compatible material is used to form a component of the sensor portion, the component being externally exposed.

6. A sensor mechanism-equipped catheter according to claim 1, wherein the sensor portion is joined to the catheter tube by an adhesive that is made of a biologically compatible material.

7. A sensor mechanism-equipped catheter comprising:
   a catheter tube; and
   a sensor portion including a pressure-receiving portion disposed at a distal end side of the catheter tube, a pressure-transmitting medium, a pressure sensing means, and a joining member that fixes the pressure sensing means in the sensor portion, the joining member being formed by disposing a fluidal material and hardening the fluidal material, the joining member also serving as a pressure barrier wall that prevents the pressure-transmitting medium from flowing toward a base end of the catheter tube.

8. A sensor mechanism-equipped catheter according to claim 7, wherein the sensor portion further comprises a tube member that has been formed separately from the catheter tube and that is fitted to a distal end side of the catheter tube, and wherein the pressure sensing means is fixed to an inner wall surface of the tube member by the joining member, and wherein the joining member seals a through bore of the tube member in such a manner that communication across the joining member is prevented.

9. A sensor mechanism-equipped catheter according to claim 8, wherein the pressure sensing means includes a semiconductor pressure sensor chip that is mounted on a seat member so that the sensor chip is fixed relative to a cut-out portion formed at a distal end side of the tube member.

10. A sensor mechanism-equipped catheter according to claim 9, wherein the joining member is formed from an insulating material, and seals, in an overall manner, at least a bonding wire extending from the sensor chip.

11. A sensor mechanism-equipped catheter according to claim 7, wherein the joining member is a hard member formed from a biologically compatible material.

12. A sensor mechanism-equipped catheter comprising
    a catheter tube; and
    a sensor portion disposed at a distal end side of the catheter tube that detects a pressure change, the sensor portion including a pressure-receiving portion, a pressure-sensing portion, an outer tube holding the pressure-receiving portion at a distal end side of the outer tube, and an inner tube supporting th e pressure-sensing portion at an end side of the inner tube, the inner tube being fitted into the outer tube, the sensor portion further including a fluidic pressure-transmitting medium that fills a space between the pressure-receiving portion and the pressure-sensing portion, the space being formed within the outer tube, and a pressure barrier wall that prevents the fluidic pressure-transmitting medium from flowing toward the catheter tube,
    wherein the sensor portion is provided as a unit separate from the catheter tube and is mounted at the distal end of the catheter tube, and at least one of the outer tube and the inner tube has an irregular surface that is formed in a joint portion thereof fittable to the distal end of the catheter tube.

13. A sensor mechanism-equipped catheter according to claim 12, wherein the sensor portion is provided as a unit separate from the catheter tube and is mounted at the distal end side of the catheter tube.

14. A sensor mechanism-equipped catheter according to claim 13, wherein at least one of the outer tube and the inner tube has an irregular surface that is formed in a joint portion thereof fittable to the distal end side of the catheter tube.

15. A sensor mechanism-equipped catheter according to claim 12, wherein the joint portion is formed as a base end-side small-diameter portion of the outer tube, and wherein a plurality of slip-off preventative grooves extend, in a circumferential direction, on an outer peripheral surface of the small-diameter portion.

16. A sensor mechanism-equipped catheter according to claim 12, wherein a biologically compatible material is used to form a component of the sensor portion, the component being externally exposed.

17. A sensor mechanism-equipped catheter according to claim 12, wherein the sensor portion is joined to the catheter tube by an adhesive that is made of a biologically compatible material.

18. A sensor mechanism-equipped catheter comprising:
    a catheter tube; and
    a sensor portion disposed at a distal end side of the catheter tube that detects a pressure change, the sensor portion including a pressure-receiving portion, a pressure-transmitting medium, pressure sensing means, and a joining member that fixes the pressure sensing means in the sensor portion, the joining member being formed by disposing a fluidal material and hardening the fluidal material, the joining member also serving as a pressure barrier wall that prevents the pressure-transmitting medium from flowing toward a base end of the catheter tube,
    wherein the sensor portion further comprises a tube member that has been formed separately from the catheter tube and that is fitted to a distal end side of the catheter tube and wherein the pressure sensing means is fixed to an inner wall surface of the tube member by the joining member, and wherein the joining member seals a through bore of the tube member in such a manner that communication across the joining member is prevented.

19. A sensor mechanism-equipped catheter according to claim 18, wherein the pressure sensing means includes a semiconductor pressure sensor chip that is mounted on a seat member so that the sensor chip is fixed relative to a cut-out portion formed at a distal end side of the tube member.

20. A sensor mechanism-equipped catheter according to claim 19, wherein the joining member is formed from an insulating material, and seals, in an overall manner, at least a bonding wire extending from the sensor chip.

* * * * *